United States Patent [19]

Brun

[11] 4,373,382

[45] Feb. 15, 1983

[54] METHOD OF ASCERTAINING THE HYDRATING ACTION OF A PRODUCT TO BE APPLIED TO THE SKIN

[75] Inventor: Nicole A. A. Brun, Geneva, Switzerland

[73] Assignee: Labiol S.A., Switzerland

[21] Appl. No.: 259,669

[22] Filed: May 1, 1981

[30] Foreign Application Priority Data

Jul. 9, 1980 [CH] Switzerland ............... 5242/80

[51] Int. Cl.$^3$ ................. G01N 33/15; G01N 13/00
[52] U.S. Cl. .................................... 73/53; 73/432 R
[58] Field of Search ..................... 73/73, 432 R, 53

[56] References Cited

U.S. PATENT DOCUMENTS 1,642,577  9/1927  Carson ........................... 73/73
3,028,755  4/1962  Carter ........................... 73/73

*Primary Examiner*—S. Clement Swisher
*Attorney, Agent, or Firm*—Kane, Dalsimer, Kane, Sullivan and Kurucz

[57] ABSTRACT

In this method of ascertaining the hydrating action of a product to be applied on the skin the product to be tested is applied to at least one portion of the surface of a first vegetable sample, for example an apple, and this first sample is stored together with at least another untreated sample of the same vegetable, under the same storage conditions, and the surface evolution of these samples is compared. In addition to a visual examination, the sample may be weighed to compare the loss of weight of the treated and untreated samples. With this method it is also possible to determine the irritant or toxic effect produced on the integument.

5 Claims, No Drawings

METHOD OF ASCERTAINING THE HYDRATING ACTION OF A PRODUCT TO BE APPLIED TO THE SKIN

BACKGROUND OF THE INVENTION

The present invention relates to a method of ascertaining, controlling or checking the hydrating action exerted by a product to be applied on the human or animal skin, such as cream, ointment, gel, milk, unguent, salve, powder, lotion, solution, soap, detergent, shampoo, tincture, dye and generally all substances, whether compound or simple, likely to contact the cutaneous integument.

THE PRIOR ART

Various methods have already been proposed for ascertaining evidencing and estimating the hydrating effect or action exerted by cosmetic and pharmaceutical creams or isolated substances on the skin. Most of them take advantage of the property of human or animal keratin, as normally found for instance in the corneous layer of the skin, of absorbing water and preserve its moisture content. Such measurements can be obtained both in vitro and in vivo, and utilize gravimetric, photometric, electrical, electronic and other technical procedures. These methods and procedures are carried out in laboratory and require skilled hands as well as relatively sophisticated equipments. In most instances they are not clearly and readily understood by common consumers and are all but spectacular.

One method consisting in utilizing pigskin is disclosed for example in the French Pat. No. 2,269,327. The pigskin must be cut immediately after slaughtering the animal, then prepared and preserved at a temperature of 20° C. before its actual use. The test is carried out by using laboratory equipments.

It is the essential object of the present invention to provide a method of checking the hydrating action of a product in a simple, economical, easily understood and more spectacular manner.

The method of this invention is characterized in that it comprises the steps of applying the product to be checked to at least one portion of at least one first vegetable sample, storing said first sample and at least one second untreated sample of the same vegetable substance under the same storage conditions, and finally comparing the evolution of the surface condition of said first and second samples.

The present invention is based on the principle that skin hydration is not an active phenomenon, i.e. an addition of water from the so-called hydrating product, as thought initially, but rather a decrement in the loss of water by the skin in the surrounding medium.

The vegetable selected for carrying out a same test are preferably not only of the same species but also of the same origin, of the same gathering and have approximately the same weight. Whatever the conditions in which the vegetables are stored for a given test, these conditions must be the same for all the vegetables used in a same test. The choice of reference vegetables and of the vegetables to be processed consists in drawing by lot among those available. The vegetables can be stored either under cover or in the open air, or in a thermostat-controlled room.

Various methods may be used for judging the hydrating action or more accurately stated the anti-dehydrating effect produced by the substance to be tested. The simplest method consists in making day-by-day observations of the treated and untreated vegetables either visually or photographically. According to the vegetable utilized, it will be seen that the surface thereof becomes rapidly winkled, crackled or crinkled. By comparison, if the vegetable is treated with a product having an efficient hydrating effect, the surface will remain smooth and its skin will remain taut.

This effect can be confirmed and measured quantitatively simply by weighing several times the treated and untreated vegetables at predetermined time intervals. The vegetable evolution can thus be ascertained.

Generally, the treatment is carried out only once, i.e. the first day, whereafter the stored vegetables are touched only as necessary for weighing them. However, the treatment can be repeated several times on the same sample for determining the effect produced by a repeated application corresponding for example to a weekly or daily treatment.

With the checking method of this invention it is possible to test the hydrating action of a product as a function of various climates or geographical positions, notably according to temperature, altitude, latitude, hygrometry, insolation, and other similar parameters.

Many vegetables are suitable for carrying out the method of this invention; therefore, an exhaustive list cannot be given. Fruits, notably apples and pears, constitute the preferred vegetables for the purposes of this invention, for the following reasons: they are available throughout the year at a reasonable price; their skin is relatively thin and pervious to water vapour under surrounding the conditions corresponding to those of a private house or an ordinary office; besides, the loss of moisture of these fruits, when untreated, can easily and rapidly be determined by simple weighing, i.e. in a term ranging from a few days to a few weeks; the skin of these fruits is so thin that it will wrinkle rapidly when dehydrated, so that their degree of dehydration can be estimated at a glance.

Among a large range of fruits, oranges, mandarins and other citrus fruits, bananas, peaches, prunes, apricots, tomatoes and generally all fruits undergoing a change in their external appearance and a loss of weight when dehydrated, can be used.

It is also possible to use vegetables such as potatoes, marrows, cucumbers, turnips, carrots and in general all vegetables undergoing a change in their external appearance and a loss of weight when dehydrated.

Other non-edible vegetables, such as thick-leaved plants, leaves and even certain plant flowers and wild trees and ornamental trees can also be used.

Vegetables are particularly sensitive to an irritating effect and when the product tested by means of the method of this invention is not well tolerated by the integument, the vegetable reacts in most instances by changing its color or by fading. Thus, this method, in addition to the hydrating effect, can supply information as to the irritant or toxic effect produced on the integument by the tested substance. To sum up, the method of this invention is characterized by the following advantages:

The method is economical, since it dispenses with expensive equipment and skilled personnel, so that it is applicable directly by the consumer;

The result can be checked visually, without any handling or measurement;

The result can be translated quantitatively by weighing;

With this method the irritant or toxic effect produced by the substances being tested on the integument can be checked simultaneously;

By utilizing vegetables as testing material according to the method of the present invention, any test on animals is definitely avoided.

Finally, the result is particularly spectacular and lends itself particularly well to advertising and marketing purposes.

The invention will now be explained with reference to a few examples.

EXAMPLE I

Testing a Hydrating Cream

Ten apples of the Golden delicious species in a perfect condition (i.e. without any trace of blows, and with a spotless skin), are rinsed with care in cold water to remove any dust and impurities, and then dried carefully by using clean cloth. The ten apples are divided into two groups of five each by drawing by lot. Each apple is numbered and weighed. Each apple belonging to the group to be treated is coated with H cream to be extent necessary for coating a hand, i.e. about 1.5 grams of cream spread all over the apple surface, without omitting the stalk cavity. Then the ten apples are disposed side by side in a room sheltered from air current and direct sunbeams, under temperature and moisture conditions similar to those of an ordinary flat. The apples are photographed the first day; then once a week. They are weighed every other day. After 28 days, the apples coated with H cream retained their original aspect and their average loss of weight was about 8.5%. On the other hand, the apples forming the untreated group are wrinkled, shrivelled and lost about 21% if their weight in the average.

EXAMPLE II

Testing a Hydrating Milk

Twelve William pears are rinsed and dried with care, and then divided into two groups of six. The pears of the group to be treated are coated with a G hydrating milk. The twelve pears are weighed after one hour, then stored in a room sheltered from air currents and direct sunbeams. The pears are photographed the first day, whereafter they are weighed and photographed every other weeks. After six weeks, the pears of the treated group begin to wrinkle very moderately on their skin surface, and the pears of the reference group are already considerably wrinkled and shrivelled. The average loss of weight of the treated pears was 14.1% and the average loss of the untreated or reference pears was 27.8%.

EXAMPLE III

Comparison Between the Anti-dehydrating Activity of Two Creams

Twelve first-quality apples of the Canadian Rennett species, having a spotless skin free of any marks or blows, after careful rinsing and drying steps, are divided into three groups of four by drawing by lot, and numbered. The apples of group I are coated with a face cream M, those of group II with a cream P advertised as "super-hydrating". The apples of group III are not treated. The twelve apples are weighed 90 minutes after the treatment and photographed. Then, they are laid side by side in the open air but sheltered from weather conditions and sunbeams. The temperature varies withing the range of 6° to 22° C. The apples are weighed every five days and photographed each week. After five weeks, the apples of group III are strongly shrivelled, and lost in the average 22.7% of their initial weight. Those of group II are almost as wrinkled as those of group III, and lost in the average 20.4% of their initial weight. On the other hand, those of group I are almost wrinkle-free and lost only 12.6% of their initial weight, in the average. This amply proves the considerable difference in anti-dehydrating activity between creams M and P, the latter having a nearly zero activity and the former an obvious activity, since it reduces by nearly 50 percent the loss of water of the tested apples.

What is claimed is:

1. Method of ascertaining the hydrating effect of a product to be applied on the skin, which comprises the steps of applying the product to be tested on at least one portion of at least one first sample of a vegetable, storing this first sample and at least another sample of the same vegetable but untreated under the same storage conditions, and finally comparing the evolution of the surface condition of the first and second samples.

2. The method of claim 1, wherein the weights of the first and second samples are compared at the end of the storage period.

3. The method of claim 1, wherein the first and second samples are weighed at predetermined time intervals and the evolution of the measured weights is compared.

4. The method of claim 1, wherein the steps are repeated several times on the same sample to determine the effect resulting from a repeated application of the product to be tested.

5. The method of claim 4, wherein vegetables of the same species, from the same gathering and having approximately the same weights are used.

* * * * *